(12) United States Patent
Shenfarber et al.

(10) Patent No.: US 11,090,506 B2
(45) Date of Patent: Aug. 17, 2021

(54) DISPOSABLE PRODUCT CAP AND ASSEMBLY HAVING A MANUALLY USABLE THERMO-OPTICAL DEVICE FOR SKIN CARE

(71) Applicant: OMM IMPORTS INC., Doral, FL (US)

(72) Inventors: Moti Shenfarber, Miami Beach, FL (US); Gennadiy Berinsky, Modein (IL)

(73) Assignee: Omm Imports, Inc., Doral, FL (US)

(*) Notice: Subject to any disclaimer, the term of this patent is extended or adjusted under 35 U.S.C. 154(b) by 518 days.

(21) Appl. No.: 15/980,336

(22) Filed: May 15, 2018

(65) Prior Publication Data
US 2019/0351251 A1 Nov. 21, 2019

(51) Int. Cl.
| | |
|---|---|
| *A61N 5/06* | (2006.01) |
| *A61K 8/9789* | (2017.01) |
| *A61K 8/92* | (2006.01) |
| *A45D 40/00* | (2006.01) |
| *A45D 34/04* | (2006.01) |
| *A61Q 19/00* | (2006.01) |
| *A45D 34/00* | (2006.01) |

(52) U.S. Cl.
CPC .......... *A61N 5/0616* (2013.01); *A45D 34/04* (2013.01); *A45D 40/00* (2013.01); *A61K 8/922* (2013.01); *A61K 8/9789* (2017.08); *A61N 5/062* (2013.01); *A61N 5/0625* (2013.01); *A61Q 19/00* (2013.01); *A45D 2034/005* (2013.01); *A45D 2040/0012* (2013.01); *A45D 2200/05* (2013.01); *A45D 2200/155* (2013.01); *A45D 2200/205* (2013.01); *A45D 2200/25* (2013.01); *A61K 2800/81* (2013.01); *A61N 2005/063* (2013.01); *A61N 2005/0644* (2013.01); *A61N 2005/0652* (2013.01)

(58) Field of Classification Search
CPC ...... A45D 34/04; A45D 40/00; A61N 5/0616; A61N 5/062; A61N 5/0625; A61K 8/9789; A61K 8/922
See application file for complete search history.

(56) References Cited

U.S. PATENT DOCUMENTS

| | | | | |
|---|---|---|---|---|
| 2,853,728 | A | * | 9/1958 | Alexander Nadai .. B65D 47/42 401/202 |
| 4,427,001 | A | | 1/1984 | Kiefer et al. |
| 4,739,778 | A | * | 4/1988 | Christie ............ A45D 40/0087 132/320 |
| 5,042,690 | A | * | 8/1991 | O'Meara ............. A45D 34/042 206/15.2 |
| 7,204,846 | B2 | | 4/2007 | Suzuki |
| 8,321,008 | B2 | * | 11/2012 | Petersen .................. A61N 1/30 604/20 |
| 9,808,646 | B2 | * | 11/2017 | Piergallini ................ A61P 1/02 |

(Continued)

*Primary Examiner* — Nicholas D Lucchesi
(74) *Attorney, Agent, or Firm* — The Concept Law Group, PA; Scott D. Smiley; Scott M. Garrett

(57) ABSTRACT

A cap to be placed on a head of a device for treating the skin of a user includes an inner part to be removably attached to the head of the device, an outer part to be placed against the skin of the user and an interior disposed between the inner and outer parts. A product is disposed in the interior for application to the skin of the user and a covering, such as a membrane which is disposed on the outer part or a sterilized pack, is removable before use. An assembly having the device and the cap is also provided.

16 Claims, 2 Drawing Sheets

(56) References Cited

U.S. PATENT DOCUMENTS

| | | | |
|---|---|---|---|
| 9,872,813 B2 | 1/2018 | Giraud et al. | |
| 2002/0055702 A1* | 5/2002 | Atala | A61M 37/0092 604/20 |
| 2003/0083618 A1* | 5/2003 | Angel | A61M 5/155 604/141 |
| 2003/0120185 A1 | 6/2003 | Dirks et al. | |
| 2003/0123919 A1* | 7/2003 | Gueret | A45D 34/00 401/130 |
| 2006/0058714 A1* | 3/2006 | Rhoades | A45D 34/04 601/73 |
| 2007/0019004 A1 | 1/2007 | Ghislain Bossut et al. | |
| 2007/0032843 A1* | 2/2007 | Hsu | A61N 5/06 607/88 |
| 2009/0260567 A1* | 10/2009 | Ozuna | A61M 37/0076 118/600 |
| 2010/0274162 A1 | 10/2010 | Evans | |
| 2013/0158547 A1* | 6/2013 | David | A61B 17/00 606/41 |
| 2014/0021654 A1* | 1/2014 | Martins | B29C 59/16 264/400 |
| 2014/0135798 A1* | 5/2014 | David | A61H 7/005 606/131 |
| 2014/0219701 A1 | 8/2014 | Eberlein | |
| 2014/0330289 A1* | 11/2014 | Revivo | A45D 34/04 606/131 |
| 2014/0376984 A1* | 12/2014 | Villarreal | A45D 34/04 401/2 |
| 2016/0038402 A1* | 2/2016 | Lahousse | A61K 8/893 424/64 |
| 2017/0312490 A1* | 11/2017 | Unger | A61M 37/0092 |
| 2018/0027950 A1* | 2/2018 | Choi | B01F 15/0237 |
| 2019/0200726 A1* | 7/2019 | Shinoda | A45D 44/002 |
| 2019/0335877 A1* | 11/2019 | Lee | B65D 35/38 |
| 2020/0093945 A1* | 3/2020 | Jeong | A45D 44/02 |

\* cited by examiner

DISPOSABLE PRODUCT CAP AND ASSEMBLY HAVING A MANUALLY USABLE THERMO-OPTICAL DEVICE FOR SKIN CARE

BACKGROUND OF THE INVENTION

Field of the Invention

The invention relates to a disposable product cap for manually usable thermo-optical devices for applying products, such as creams or lotions, to the skin. The invention also relates to an assembly having the device and the cap.

Description of the Related Art

There is a wide range of instruments for home use and cosmetology institutes which are constructed to treat the skin with light, heat, ultrasound and a combination thereof.

In some cases, before or after treatment, substances are applied manually for various purposes, such as increasing the effectiveness of the treatment, calming the skin from the treatment of lye, disinfecting and improving the treatment experience, etc.

Handheld devices having LEDs are known for using light therapy to treat wrinkles and discoloration of the skin. Such devices may emit invisible infrared rays that penetrate below the surface of the skin, promote collagen, reduce wrinkles and fine lines and restore elasticity.

U.S. Patent Application Publication 2014/0219701 A1 discloses a temperature modulating device 100 having a temperature modulating device element 106, a built-in applicator 102 for a fluid and a protective cap 112 to be applied when not in use.

U.S. Patent Application Publication 2010/0274162 A1 shows a massager 10 with a massage head 48, a fluid reservoir 44 and a temperature band 46 for heating and cooling a massage roller ball 42.

U.S. Patent Application Publication 2007/019004 A1 teaches a photocosmetic device with attachments 810, 820, such as a pad, for distributing lotion, etc., such as in FIG. 32 and paragraph [0187].

U.S. Patent Application Publication 2003/0120185 A1 discloses a massager 10 having a heated applicator pad 28 and a pocket 34 for an enhancement pad 36.

U.S. Pat. No. 9,872,813 B2 shows a messaging head 1 of an appliance A having a massaging finger 21 with a cap 67 forming a work head 22. A pad 68 may be soaked in a cosmetic product so that the product is dispended by the cap.

U.S. Pat. No. 9,808,646 B2 teaches a therapy device 30 having an applicator cartridge 10 with a head 12 and a reservoir 14 delivering for a composition which is photoactive.

U.S. Pat. No. 7,204,846 B2 discloses a device 1 having a base portion 19 covered with a cloth 19 and a cotton holder carrying a solution.

U.S. Pat. No. 4,427,001 shows a massager 10 including a main body 11 with a reservoir 19 having a filter opening 20. Dispensing of oil or cream is carried out through openings 22 into a sponge 23 and against rollers 24.

It is therefore seen that many devices have reservoirs containing a product or pads which are soaked in a product. However, the reservoirs are messy and difficult or impossible to clean and they make the device much more complicated and expensive. Pads are messy and hard to keep in place. There is therefore a need for a way of distributing the product which is easily applicable outside the device and yet stays in place.

BRIEF SUMMARY OF THE INVENTION

It is accordingly an object of the invention to provide a disposable product cap and an assembly having a manually usable thermo-optical device for skin care, which overcome the hereinafore-mentioned disadvantages of the heretofore-known devices and assemblies of this general type and in which the disposable cap is temporarily affixed to the device and distributes the product.

The invention is constructed to combine the product, such as a cream, with the head of a device while avoiding smearing, helping in the controlled release of the product or cream, combining the effect of heat and the effect of optical energy during treatment and facilitating the smoothness of the device on the surface of the skin.

Invention makes it easy to use a wide variety of cosmetic preparations and helps to keep the device clean and hygienic.

With the foregoing and other objects in view there is provided, in accordance with the invention, a cap to be placed on a head of a device for treating the skin of a user. The cap comprises an inner part to be removably attached to the head of the device, an outer part to be placed against the skin of the user, an interior disposed between the inner and outer parts, a product disposed in the interior for application to the skin of the user, and covering such as a membrane being disposed on the outer part or a sterilized pack, both being removable before use. Therefore, the invention provides a way of distributing the product by using a cap which is easily applicable outside the device and yet stays in place.

In accordance with another feature of the invention, a reinforcing ring which is disposed on the inner part is configured to be attached to the head of the device. The reinforcing ring not only strengthens the cap but provides an attachment to the device.

In accordance with a further feature of the invention, the membrane has a tab facilitating removal of the membrane. The tab furthers the object of reducing the messiness of product application.

In accordance with an added feature of the invention, the cap is made from a material that conducts heat and is transparent along a wavelength of the device, permitting heat and light from the device to pass through the cap and the product disposed therein.

In accordance with an additional feature of the invention, the cap has a surface being transparent, matte or having optical properties defined by a different surface.

In accordance with yet another feature of the invention, the cap surface acts as a Fresnel or micro raster lens to control light scattering and adhesion of the product on the skin of the user.

In accordance with yet a further feature of the invention, the product is provided as a whole layer, in points, in rings or in another non-continuous geometrical form allowing penetration of light during use of non-transparent creams as the product.

In accordance with yet an added feature of the invention, a melting point of the product is adjusted to heat produced by the device to achieve a slow release.

In accordance with yet an additional feature of the invention, the chemical properties, color and viscosity of the product are modified in a predefined manner as a result of integration with light and heat waves from the device.

These features ensure that the product is applied in an optimal manner.

In accordance with again another feature of the invention, the membrane includes trade mark information, content information or instructions for use. This ensures that the user of the device has chosen the cap with the desired product contained therein.

In accordance with again a further feature of the invention, the cap has an optical or magnetic mark allowing identification of the cap and the product contained therein. The cap can therefore be machine-readable for inventory and billing purposes, etc.

In accordance with again an added feature of the invention, the cap is disposable. The user can discard the entire cap after use, thus reducing clean-up time an effort.

In accordance with an added feature of the invention, the product is selected from the group consisting of day cream, night cream, lotion cream and mood cream.

In accordance with an added feature of the invention, the head of the device has LEDs emitting light. Such devices are commonly used for skin treatment and may be used with the cap of the invention.

With the objects of the invention in view, there is concomitantly provided a skin treatment assembly, comprising a device for treating the skin of a user, the device having a head which may have LEDs, and a cap to be placed on the head of the device. The cap includes an inner part to be removably attached to the head of the device, an outer part to be placed against the skin of the user, an interior disposed between the inner and outer parts, a product disposed in the interior for application to the skin of the user and a membrane being disposed on the outer part and being removable before use. The advantages of the cap described above are equally applicable to the assembly which includes the cap.

Other features which are considered as characteristic for the invention are set forth in the appended claims.

Although the invention is illustrated and described herein as embodied in a disposable product cap for manually usable thermo-optical devices, it is nevertheless not intended to be limited to the details shown, since various modifications and structural changes may be made therein without departing from the spirit of the invention and within the scope and range of equivalents of the claims.

The construction and method of use of the invention, however, together with additional objects and advantages thereof will be best understood from the following description of the specific embodiment when read in connection with the accompanying drawings.

DETAILED DESCRIPTION OF THE INVENTION

Figure 1:
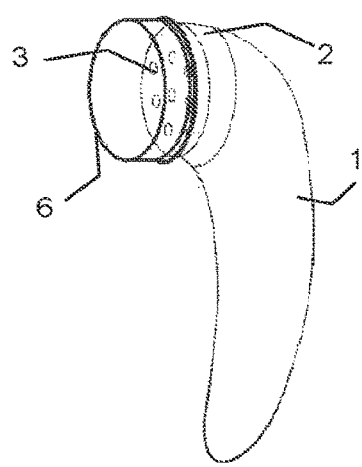
FIG. 1 is a diagrammatic, perspective view of a handheld LED device with the product cap according to the invention.

Referring now to the figures of the drawing in detail and first, particularly, to FIG. 1 thereof, there is seen a handheld device 1 having a head 2 with LEDs 3 and a product cap or capsule 6. The device may be the Perfectio by Zero Gravity, which emits red LED light, or a similar device.

Figure 2:
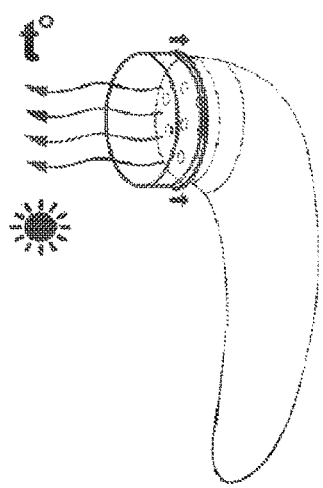
FIG. 2 is a perspective view of the handheld LED device having the product cap and indicating light and heat to be applied to the skin.

The product or cream cap 6 is made from a material that conducts heat and is transparent along the wavelength of the device. It can therefore be seen in FIG. 2 that heat and light from the device 1 pass through the product cap 6 and the product disposed therein.

Figure 3:
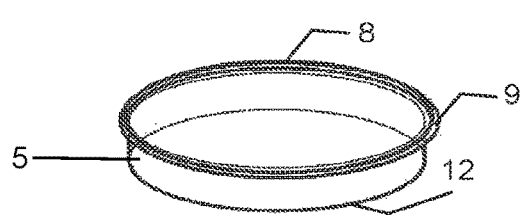
FIG. 3 is a perspective view of an empty product cap.

As is seen in FIG. 3, the product cap 6 has an inner part with 8 with a reinforcement ring 9 which is to be attached to the head 2 of the device 1 and keeps the head 2 of the device 1 clean. The inner part 8 with the reinforcement ring 9 may be snapped over the head 2 or otherwise held in position, such as by screw threads, a layer of adhesive or a bayonet connection. The reinforcement ring 9 is located at the bottom of a sidewall 5 that extends from the outer part 12, which faces toward the user's skin, at an edge 18 of the outer part 12 and around an entirety of the outer part 12, and perpendicular to the outer part 12.

Figure 4A:
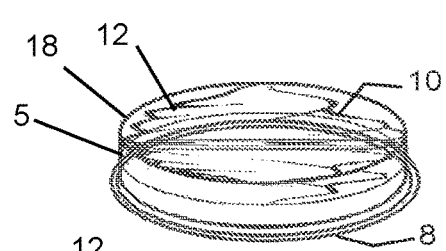
FIGS. 4A, 4B and 4C are respective perspective, vertical-sectional and perspective views of a product cap filled with a product to be applied to the skin and a sterilized pack for holding the product cap.
Figure 4B:
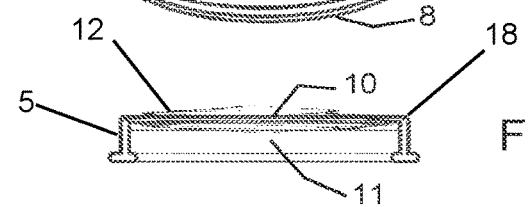

FIGS. 4A and 4B show that a layer 10 of a product, such as a cream, oil or lotion, is disposed in an interior 11 of the cap 6 between the inner part 8 and an outer part 12 facing towards the skin.

Figure 4C:
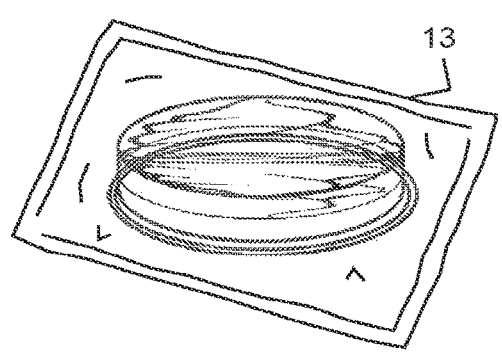

FIG. 4C shows that the cap 6 containing the product 10 may be held in a covering in the form of a sterilized pack 13 which is shown as being torn open in the figure.

The product or cream can be provided in as a whole layer, in points, in rings and in any other non-continuous geometrical form which allows penetration of light in the use of non-transparent creams.

The melting point of the cream can be adjusted to the heat of the device in order to achieve a slow release. A slow release is made possible due to a complex of distinct waxes with different melting points. For instance, candellila wax with a melting point of 60° C.-70° C. and shea butter with a melting point of 35° C. may be used in a ratio of 13:1. As long as the 13:1 wax ratio is maintained, the cream will start to melt at 40° C. so that it never becomes fluid, although the viscosity decreases.

The chemical properties, color, and viscosity of the cream can be modified in a predefined manner as a result of integration with light and heat waves. Regarding the color, the cream is white, but when melting on the skin it appears transparent. No change is observed in the timeline of the cream (before it is placed on the device and after heating). U.S. Pat. No. 4,996,044 refers to lipstick formulation and describes a process which is similar to the process employed for the product used in the present invention.

Figure 5A:
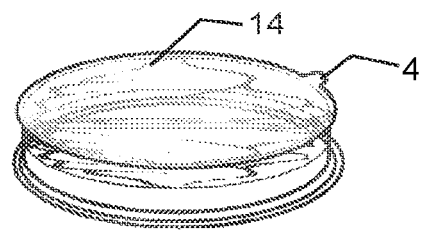
FIGS. 5A and 5B are respective perspective and vertical-sectional views of a product cap filled with a product to be applied to the skin and having a removable membrane.
Figure 5B:
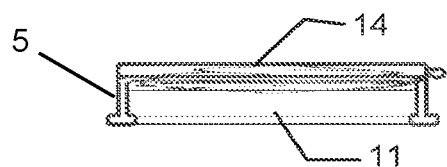

As is seen in FIGS. 5A and 5B, the outer part or top 12 of the cap 6 has a covering in the form of a membrane 14 that needs be removed before beginning to use the cap 6. The membrane 14 has a tab 4 that extends outward beyond the sidewall 5 making it easier to remove. The membrane 14 is used as an alternative or in addition to the sterilized pack 13 shown in FIG. 4C as different coverings.

Figure 6A:
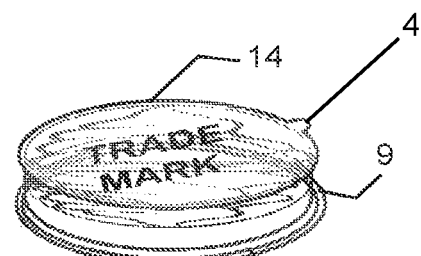
FIGS. 6A and 6B are respective perspective and vertical-sectional views of a product cap filled with a product to be applied to the skin and having a removable membrane with identifying indicia.
Figure 6B:
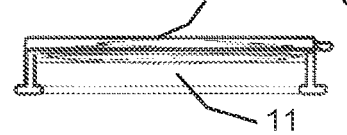

This membrane 14 can include trade mark information or any other information, such as the contents of the cap 6 or instructions for use, as is shown in FIGS. 6A and 6B.

Figure 7A:
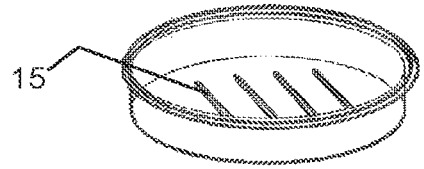
FIGS. 7a and 7b are perspective views of an empty product cap similar to FIG. 3 but respectively having Fresnel and micro raster lenses.
Figure 7B:
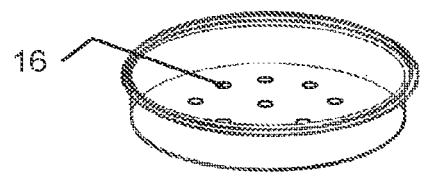

The surface of the cap 6 may be transparent, matte or with optical properties defined by a different surface such as a Fresnel lens 15 or a micro raster lens 16 to control light scattering and cream adhesion on a surface, as shown in FIGS. 7A and 7B.

Figure 8:
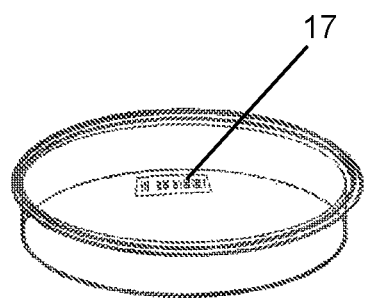
FIG. 8 is a perspective view of an empty product cap similar to FIG. 3 but with an optical or magnetic mark for identification purposes.

FIG. 8 shows that the cap 6 may have an optical or magnetic mark 17 at any location that allows the identification of the cap and the contents thereof.

The product or cream cap 6 is disposable. Prior to use, the cream cap 6 stays in closed packaging 13, 14 and permits easy preservation and selection between different types of products or creams in the caps 6. As an example: day cream, night cream, lotion cream, or mood cream may be provided.

Useful product and marketing information about the cream and its characteristics can be printed on the packaging 13, 14. After removing the cap 6 from the package 13, 14, the cap 6 is placed on top of the device 1 and the device or appliance 1 is turned on.

The sterilized pack 13 or the membrane 14 for protecting the product or cream is then removed and after respectively tearing it open or pulling it off, the cap 6 is ready for use.

Heat and light from the device 1 penetrates through the cap since the cap 6 is transparent along the wavelength of the device. The heat melts the cream and causes a controlled release. The transparency of the cap allows for an optimum therapeutic effect of the device.

During use, the user moves the device over the skin, gradually rubbing the cream into the skin. The heat of the device in combination with the cream helps to increase the effect of the action.

After using cap 6, it is removed from the appliance or device 1 and discarded.

The invention claimed is:

1. A cap to be placed on a head of a device for treating the skin of a user, the cap comprising:
   an inner part to be removably attached to the head of the device;
   an outer part to be placed against the skin of the user;
   a sidewall that extends from the outer part at an edge of the outer part around an entirely of the outer part, and perpendicular to a surface of the outer part;
   a reinforcing ring at a bottom of the sidewall on the inner part that is sized to retain the cap on the head of the device;
   an interior disposed between said inner and outer parts;
   a product disposed in said interior for application to the skin of the user; and
   a covering being disposed on said outer part and being removable before use.

2. The cap according to claim 1, wherein said covering is a membrane having a tab facilitating removal of said membrane.

3. The cap according to claim 1, wherein said covering is a sterilized pack to be removed before use.

4. The cap according to claim 1, wherein the cap is made from a material that conducts heat and is transparent for a wavelength of light produced by the device, permitting heat and light from the device to pass through the cap and said product disposed therein.

5. The cap according to claim 1, which further comprises a cap surface being transparent, matte, or having a lens surface.

6. The cap according to claim 5, wherein the lens surface is a Fresnel or micro raster lens surface to control light scattering and adhesion of said product on the skin of the user.

7. The cap according to claim 1, wherein said product is provided as points, in rings or in another non-continuous geometrical form allowing penetration of light during use of non-transparent creams as said product.

8. The cap according to claim 1, wherein said product is a composition having a melting point of 40 degrees C.

9. The cap according to claim 1, wherein chemical properties, color and viscosity of said product are modified in a predefined manner as a result of integration with light and heat waves from the device.

10. The cap according to claim 1, wherein said covering includes trade mark information, content information or instructions for use.

11. The cap according to claim 1, which further comprises an optical or magnetic mark allowing identification of the cap and said product contained therein.

12. The cap according to claim 1, wherein the cap is disposable.

13. The cap according to claim 1, wherein said product is selected from the group consisting of day cream, night cream, lotion cream and mood cream.

14. The cap according to claim 1, wherein the head of the device has LEDs emitting light.

15. A skin treatment assembly, comprising:
   a device for treating the skin of a user, said device having a head; and
   a cap to be placed on said head of said device, said cap including:
      an inner part to be removably attached to said head of said device;
      an outer part to be placed against the skin of the user;
      a sidewall that extends from the outer part at an edge of the outer part around an entirely of the outer part, and perpendicular to a surface of the outer part;
      a reinforcing ring at a bottom of the sidewall on the inner part that is sized to retain the cap on the head of the device;
      an interior disposed between said inner and outer parts;
      a product disposed in said interior for application to the skin of the user; and
      a covering being disposed on said outer part and being removable before use.

16. The assembly according to claim 15, wherein said head of said device has LEDs emitting light.

* * * * *